United States Patent
Nakatani

[11] Patent Number: 5,928,176
[45] Date of Patent: Jul. 27, 1999

[54] MEDICAL SWAB

[76] Inventor: Hiroshi Nakatani, 7-8, Umenosato 2-chome, Tondabayashi-shi, Osaka 584-0001, Japan

[21] Appl. No.: 09/069,076

[22] Filed: Apr. 29, 1998

[51] Int. Cl.[6] .................................................. A61M 35/00
[52] U.S. Cl. .............................. 604/1; 600/572; 15/208; 15/230.13
[58] Field of Search ........................... 604/1–3; 600/572; 19/145.3; 15/230.12, 208, 203.13

[56] References Cited

U.S. PATENT DOCUMENTS

| | | | |
|---|---|---|---|
| 3,542,025 | 11/1970 | Gustafson | 19/145.3 |
| 3,586,380 | 6/1971 | Albeckoff | 604/1 |
| 3,923,061 | 12/1975 | Rossingnol | 604/1 |
| 4,306,555 | 12/1981 | Ritter | 600/572 |
| 4,994,325 | 2/1991 | Moteki et al. | 604/1 |
| 5,078,943 | 1/1992 | Moteki et al. | 264/209.5 |

FOREIGN PATENT DOCUMENTS

| | | |
|---|---|---|
| 60-19921 | 5/1985 | Japan . |
| 7-189103 | 7/1995 | Japan . |

*Primary Examiner*—John G. Weiss
*Assistant Examiner*—Dennis Ruhl
*Attorney, Agent, or Firm*—Sughrue, Mion, Zinn, Macpeak & Seas, PLLC

[57] ABSTRACT

There is provided a medical swab comprising a thin stick comprising a drawn plastic stick and a sphere-like fiber lump formed on at least one end of the stick; the fiber lump has a fiber winding portion which is formed by winding a part of the fibers around the stick and then is fixed to the stick either by using an adhesive, or by tightening the fiber lump containing a fibrillating cellulose without using an adhesive.

3 Claims, 2 Drawing Sheets

MEDICAL SWAB

BACKGROUND OF THE INVENTION

1. Field of the Invention

The present invention relates to a medical swab mainly for use in medical treatments of ear, nose and the like.

2. Description of the Background Art

In medical treatments of ear, an absorbent cotton is wound around the end of a thin stainless steel stick having a diameter of about 1–1.5 mm, and the cotton is then inserted in an acoustic meatus to remove a liquid matter accumulated there, e.g., pus. Alternatively, cotton is impregnated with a medical fluid which is applied to a diseased part of the acoustic meatus. A doctor or a nurse winds cotton around the end of a stick by hand whenever it is used. The spent cotton is removed and the shaft is disinfected for reuse.

Winding cotton around the end of the stick is, however, time-consuming and not hygienic. If wound cotton is left for a long time, it is readily restored to the original state to come loose. In addition, reuse of the stick may increase the danger of possible infection.

Meanwhile, ordinary commercial cotton swab, which is generally used for ear cleaning at home or the like, comprises a stick made of plastic or the like, and sphere-like cotton lump(s) formed on the end(s) of the stick by winding cotton fibers around the stick. Since such cotton are of mass produciton and throw-away product, they have little or no danger of possible infection. However, the stick of the ordinary commercial cotton swab has a diameter of not less than 3 mm, and therefore, if inserted in an acoustic meatus in medical treatment, it is difficult for a doctor to observe the acoustic meatus, thereby making it hard to apply precisely a medical fluid to a diseased part.

The above stainless thin stick for medical treatment of nose or ear can be bent as required. This facilitates the medical treatment to diseased parts for which much effort is required. On the other hand, if the plastic stick for the ordinary cotton swab is bent, it may break or restore quickly, failing to maintain a bent state.

Additionally, in a cotton lump of the ordinary cotton swab, an adhesive is contained for adhesions between cottons and between cotton and a stick. It is however unfavorable that the cotton lump contains an adhesive or the like, because the cotton lump is brought into contact with a diseased part. Furthermore, when a cotton lump is impregnated with a medical fluid, the adhesive may dissolve in the medical fluid. Thus, the ordinary cotton swab using the adhesive cannot be employed for medical use.

SUMMARY OF THE INVENTION

It is a main object of the present invention to provide a medical swab that is hygienic and disposable, without efforts for winding cotton around the end of a stick and removing the wound cotton whenever it is used.

It is another object of the present invention to provide a medical swab using a plastic stick that has a thinness to conserve visibility in medical treatment and also permits a suitable bending so as to reach a diseased part to be treated.

It is still another object of the present invention to provide a medical swab whose cotton lump is formed without using an adhesive.

According to the present invention, there is provided a medical swab comprising a thin stick having a diameter of 0.7 to 2 mm which comprises a plastic stick drawn in the axial direction, so that the stick has bending elastisity and toughness enough to maintaining a bent state; and a sphere-like fiber lump formed on at least one end of the stick. The fiber lump has a fiber winding portion formed by winding a part of the fibers around the stick. The fiber winding portion is fixed to the stick with an adhesive.

To prevent the winding of the fiber winding portion from coming loose, the fiber winding portion is adhered to the stick with the adhesive. On the other hand, the head of the fiber lump which is to be impregnated with a medical fluid and then brought into contact with a diseased part, does not contains the adhesive. Therefore, it is particularly suited for medical use.

According to another aspect of the present invention, there is provided a medical swab comprising a thin stick having a diameter of 0.7–2 mm which is made of a plastic stick drawn in the axial direction, so that the stick has bending elasticity and toughness enough to maintaining a bent state; and a sphere-like fiber lump formed on at least one end of the stick. The fiber lump has a fiber winding portion which is formed by winding, around the stick, a part of the fibers which contains a fibrillating cellulose. The fiber winding portion is fixed to the stick by tightening.

As the fibrillating cellulose is contained in the fibers, it is possible to prevent the fiber winding portion from coming loose due to the restoration of fiber, for a long period of time, only by tightening the fiber winding portion wound around the stick without using the adhesive.

As the fiber, a variety of natural fiber (e.g., cotton, silk and wool), regenerated fiber (e.g., rayon and cupra), or synthetic fiber (e.g., polyester fiber and polypropylene fiber) can be used, and the most preferred is cotton fiber, such as absorbent cotton. In the description given below, the term "cotton" is used as an example of fiber.

DETAILED DESCRIPTION OF THE INVENTION

Figure 1:
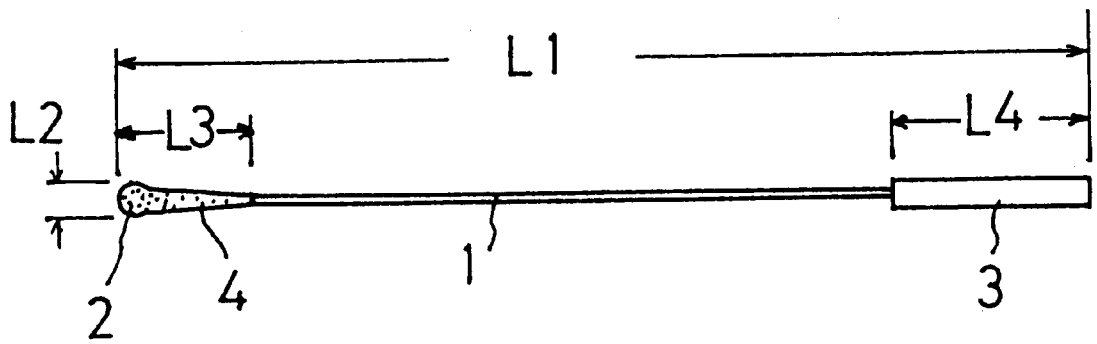
FIG. 1 is a front view of a swab according to a preferred invention of the present invention.

As shown in FIG. 1, a swab comprises a stick 1, a cotton lump 2 formed on one end of the stick 1, and a plastic handle 3 attached to the other end of the stick 1. The handle 3 is not necessarily required. In place of the handle 3, the cotton lump 2 may be provided.

The stick 1 is a thin plastic stick drawn in the axial direction, and has a diameter from 0.7 to 2 mm. Since the plastic stick is drawn in the axial direction, it has bending elasticity and toughness. Therefore, its bending elasticity is approximately equal to that of a conventional stainless steel stick, thereby causing no uncomfortableness at the time of use. In addition, the stick 1 is tough and thus resistant to bending, and can maintain a bent state. It is therefore possible to bend the stick 1 as desired, depending on a diseased part. Accordingly, the stick 1 in the present invention exhibits properties similar to those of the ordinary stainless steel stick.

As the material of the plastic stick, there are, for example, polypropylene, polystyrene, acrylonitrile-butadiene-styrene copolymer (ABS resin), polyethylene, polyvinyl chloride, polycarbonate, polyamide, and polyester. The plastic stick is drawn about five to twenty times, preferably seven to fifteen times in the axial direction. As a result, the molecules are oriented in the axial direction to increase the crystallinity, thereby obtaining the plastic stick having a high bending elasticity and strength.

The diameter of the stick 1 is in the range from about 0.7 to 2 mm, as described above, preferably about 1.1 to 1.7 mm. When the diameter of the stick 1 is larger than the above range, the visibility in medical treatment may be obstructed. When the diameter was smaller than the above range, the stick 1 may be lowered in the strength. The length of the stick 1 is generally in the range from about 10 to about 20 cm.

Figure 2:
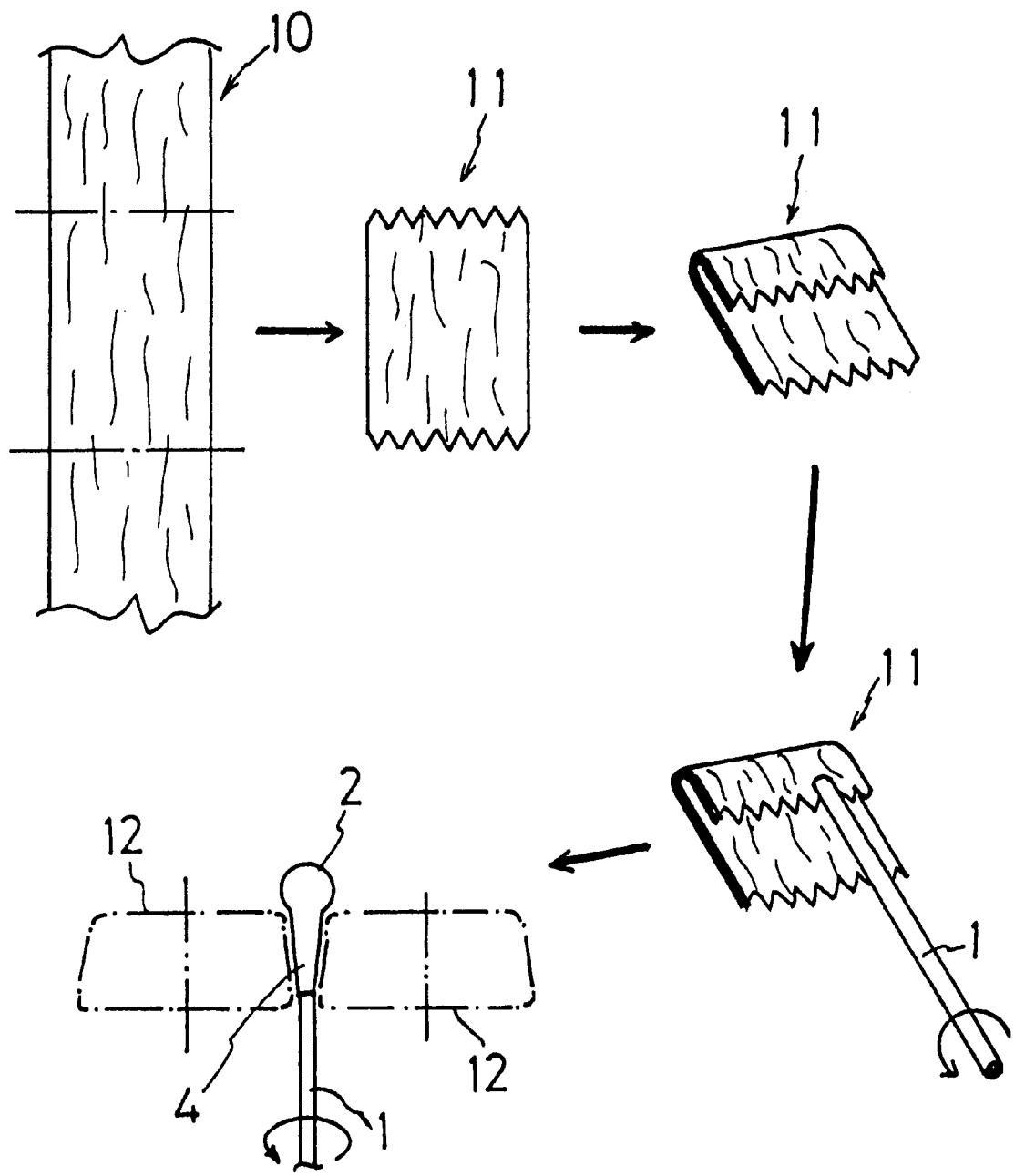
FIG. 2 is a diagram for explaining the steps of forming a fiber lump.

The cotton lump 2 is made of a sheet-shaped cotton fibers (hereinafter, called as a cotton web) 11 cut into a specific length, as shown in FIG. 2. The cotton lump 2 has a cotton winding portion 4 which is formed by winding part of the cotton web 11 around the stick 1. The cotton winding portion 4 is fixed to the stick 1 by using the adhesive. A maximum diameter (i.e., L2 in FIG. 1) of the cotton lump 2 is preferably about 3 to 7 mm.

The length of the cotton lump 2 (i.e., L3) is preferably in the range from about 10 to 30 mm. Here, a spherical head is about 20 to 60%, preferably about 30 to 50%, to the entire length (L3).

To form the cotton lump 2, the method as shown in FIG. 2 can be employed. An example of the material cotton is a strip cotton 10 which is a long strip web wherein fibers are disposed in the longitudinal direction. The strip cotton 10 is cut perpendicular to the fiber direction (the cut lines are indicated by alternate long and short dash lines), to obtain a sheet-shaped cotton web 11 (i.e., called as a "cut cotton") with a proper length. It is desirable that the strip cotton 10 is cut so as to have a non-straight edge, e.g., a shape of sawtooth or a shape obtained by tearing.

Then, one end of the web 11 is folded inward and wound around the end of the stick 1. An adhesive is applied to the cotton winding portion 4 to be in contact with the stick 1, which is then tightened by a pair of tightening rollers 12, 12, thereby fixing it to the stick 1.

At that time, it is possible to prevent the fiber from dropping out because the fibers of the cotton web 11 are disposed in the axial direction.

As the adhesive, it is preferable to use those having high safety, such as carboxylmethylcellulose, polyvinyl alcohol and shellac.

When the adhesive is not used, a fibrillating cellulose is added into the cotton web 11 in the range from 3 to 100% by weight. Then, the web 11 is wound around a stick 1 and tightened from outside by using the rollers 12 or the like, in the same manner as described above. As a result, the fibers are firmly entangled, thereby maintaining the tightened shape.

The fibrillating cellulose is obtained by fibrillating a natural cellulose fiber such as pulp or cotton. As a method of fibrillating, various methods are known. According to this invention, it is preferable to employ nd methods capable of fibrillating, namely obtaining a state that the cellulose fiber is teared mainly along a fiber axis direction can be employed. The fibrillating cellulose is disclosed in Japanese Laid-open Publication Nos. 56-100801, 63-196790, 1-249133 and 1-249843, and various products are commercially available.

The kind of fibrillating cellulose is not limited, and various fibrillating cellulose can be used. It may be preferable that the fibrillating cellulose has a fiber length of 1 to 10 mm.

To add the fibrillating cellulose to the fiber lump, the fibrillating cellulose is dispersed in a liquid such as water (or hot water) by stirring, and then the fiber web or lump is soaked in the obtained dispersion liquid of the fibrillating cellulose. Alternatively, the above dispersion liquid of the fibrillating cellulose is sprayed to the fiber web or lump.

The swab thus prepared is subjected to a sterilization using such as ethylene oxide gas or radiation, as required, and then packed.

The swab of the present invention has the following advantages.

(i) Since the cotton lump is previously formed on at least one end of the stick in factory-production, it is unnecessary for a doctor or nurse to wind a cotton around the stick in a medical treatment site. Therefore, it is time saving and hygienic;

(ii) Since the swab is disposable, it is hygienic and free from the danger of possible infection due to reuse;

(iii) Complete incineration is possible, because the stick comprises plastic;

(iv) It is suited for medical use because application of the adhesive is limited to the cotton winding portion to be in contact with the stick, and the head of the cotton lump consists of cotton fiber without any foreign matter;

(v) The cotton lump can be formed in a simple manner in which one end of a sheet-shaped cotton web is folded and wound around the stick, and only the winding portion is fixed with an adhesive. In addition, no fiber restoration occurs after the cotton lump is formed, and the fiber is firmly fixed to the stick, causing no fallout of the cotton spere;

(vi) It is possible to bend the stick suitably according to a diseased part to be treated, and to secure a doctor's view in a medical treatment because the stick is thin;

(vii) Attachment of a handle to one end of the stick increases the convenience even if the stick is thin; and (viii) It is possible to produce the swab in a simple manner at low price.

EXAMPLES

The following examples illustrate the preferable swab of the present invention.

Example 1

A drawn reinforced polypropylene stick having a diameter of 1.4 mm and a length (L1) of 150 mm, was used as a stick 1. According to the manner shown in FIG. 2, a cotton web cut into a specific length was wound around one end of the stick 1. Thereafter, an adhesive composed of carboxylmethylcellulose sodium was applied only to a cotton winding portion 4 to be in contact with the stick 1, and then tightened by a pair of rollers 12, 12. A plastic handle 3 (30 mm in length L4) was attached to the other end of the stick 1. The obtained swab was subjected to a sterilization using ethylene oxide gas.

Example 2

A swab was obtained in the same manner as that in Example 1, except that no adhesive was used and a sheet-shaped cotton web 11 obtained by uniformly mixing 95% by weight of an absorbent cotton with 5% by weight of a fibrillating cellulose was used.

In the swabs of Examples 1 and 2, the cotton lump 2 was firmly fixed to the stick so that it could not be fallen out easily. The fibers wound around the stick 1 did not restore, and no fiber fell out at the time of use.

As to bending strength, bending elasticity and toughness, there was no significant difference between the stick 1 and the conventional stainless steel stick. Also, there was no uncomfortableness at the time of use. When the stick 1 was bent at about angles of 30°, 45° and 90°, no breakdown occurred and the bent shapes were maintained.

What is claimed is:

1. A medical swab comprising:

a thin stick having a diameter of 0.7 to 2 mm and comprising a plastic stick drawn in the axial direction, so that the stick has bending elasticity and toughness enough to maintain a bent state; and a sphere-like fiber lump formed on at least one end of the stick, the fiber lump having a fiber winding portion formed by winding a part of the fibers around the stick, and the fiber winding portion being fixed to the stick with an adhesive, wherein the fiber lump is formed by winding, around the stick, sheet-shaped fibers wherein each fiber is disposed in the axial direction of the stick.

2. The medical swab of claim 1 wherein the fiber lump is formed on one end of the stick and a handle on the other end.

3. A medical swab comprising:

a thin stick having a diameter of 0.7 to 2 mm and comprising a plastic stick drawn in the axial direction, so that the stick has bending elasticity and toughness enough to maintain a bent state; and a sphere-like fiber lump formed on at least one end of the stick, the fiber lump having a fiber winding portion tightly wound around the stick, said fiber lump being comprised of natural cellulose fibers and fibrillating cellulose fibers firmly entangled with each other to maintain a tight engagement with the stick, and wherein said fiber lump is adhered to the stick without the use of adhesive.

* * * * *